United States Patent
Pauly

(10) Patent No.: US 6,491,941 B1
(45) Date of Patent: Dec. 10, 2002

(54) USE OF AT LEAST ONE LIPID EXTRACT OBTAINED FROM THE FRUIT SEED OF THE MIRABELLE TREE

(75) Inventor: Gilles Pauly, Nancy (FR)

(73) Assignee: Laboratoires Serobiologiques (Societe Anonyme), Pulnoy (FR)

( * ) Notice: Subject to any disclaimer, the term of this patent is extended or adjusted under 35 U.S.C. 154(b) by 0 days.

(21) Appl. No.: 09/720,456

(22) PCT Filed: Jun. 24, 1999

(86) PCT No.: PCT/EP99/04383
§ 371 (c)(1),
(2), (4) Date: Dec. 26, 2000

(87) PCT Pub. No.: WO99/66899
PCT Pub. Date: Dec. 29, 1999

(30) Foreign Application Priority Data

Jun. 25, 1998 (FR) .............................................. 98 08186

(51) Int. Cl.[7] .......................... A61F 13/00; A61K 6/00; A61K 7/06; A61K 7/075; A61K 7/025
(52) U.S. Cl. .................. 424/434; 424/401; 424/70.1; 424/70.11; 424/70.12; 424/70.16; 424/70.22; 424/70.27; 424/59; 424/64; 424/78.02; 424/78.03

(58) Field of Search ....................... 424/401, 78.02, 424/78.03, 725, 735, 64, 70.1, 70.22, 70.27, 70.12, 70.11, 70.16, 59, 434

(56) References Cited

U.S. PATENT DOCUMENTS

| 4,224,319 A | * | 9/1980 | Marcadet ................... 424/238 |
| 5,431,911 A | * | 7/1995 | Reynolds ................... 424/401 |
| 5,928,696 A | * | 7/1999 | Best et al. ................. 426/417 |

FOREIGN PATENT DOCUMENTS

| FR | 1 448 975 | 11/1966 |
| FR | 2 610 197 | 8/1988 |
| WO | WO 83/01898 | 6/1983 |

OTHER PUBLICATIONS

*Chemical Abstracts*, vol. 103, No. 15, G. Vernin et al, "Mirabelle Plum Aroma Study By CG–SM (Gos Chromatography–Mass Spectrometry) SPECMA Bank Analysis".

* cited by examiner

Primary Examiner—Thurman K. Page
Assistant Examiner—Humera N. Sheikh
(74) Attorney, Agent, or Firm—Young & Thompson

(57) ABSTRACT

The aim of the invention is to use at least one lipid extract obtained from the fruit seeds of the mirabelle tree as an agent for preparing a cosmetic product for locally active (topical) use for skin and hair, lips, mucous membranes and/or appendages of the skin.

8 Claims, 2 Drawing Sheets

Work (Nm)

Maximum force (N)

Work (Nm)

Maximum force (N)

Figure 1:
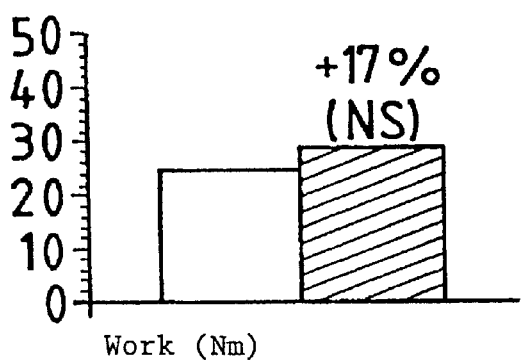
Figure 1:
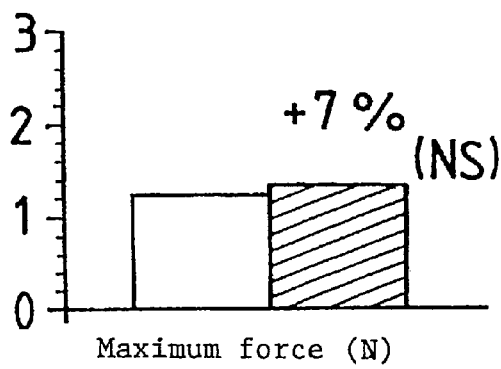
Figure 1:
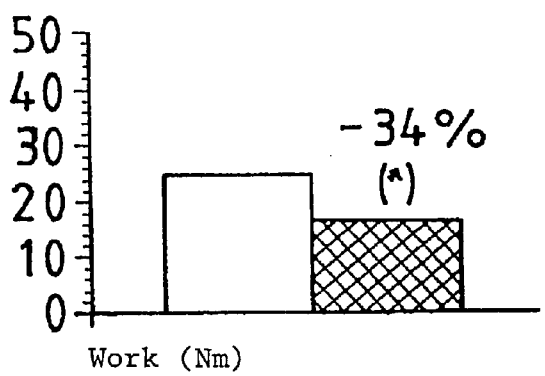
Figure 1:
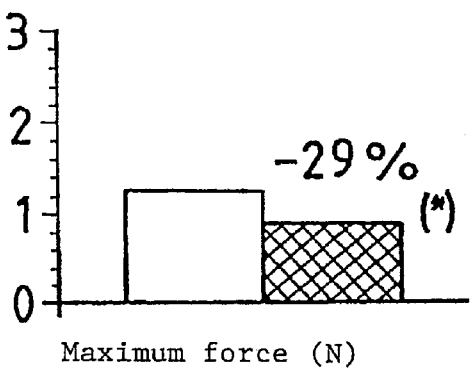

before treatment after treatment with shampoo placebo after treatment with mirabelle oil proportioned to 1.5% in a Shampoo placebo ☐ before treatment ▨ after treatment with shampoo placebo ▩ after treatment with mirabelle oil proportioned to 1.5% in a Shampoo placebo

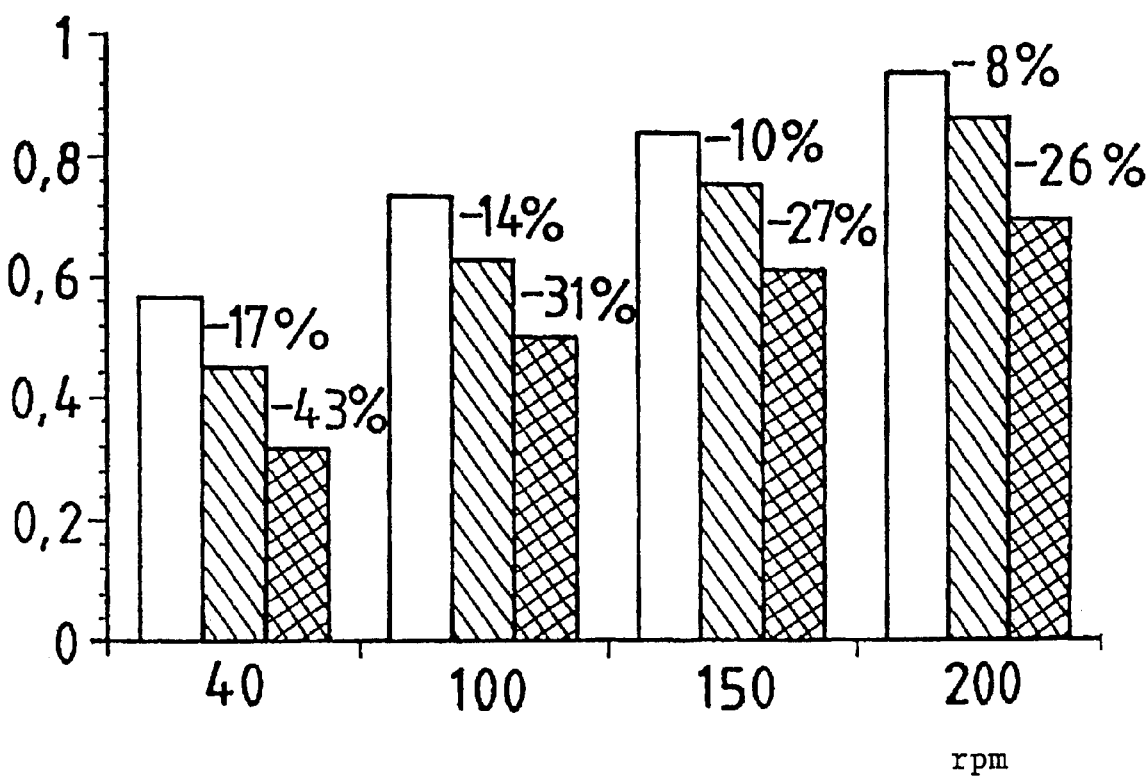
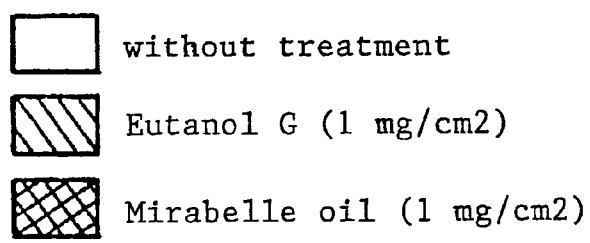

USE OF AT LEAST ONE LIPID EXTRACT OBTAINED FROM THE FRUIT SEED OF THE MIRABELLE TREE

This invention relates to the area of cosmetology, especially applications to the skin (cutaneous) and hair (capillary) and the objective is use of at least one lipid extract from the seed of the fruit of the mirabelle tree or the mirabelle in cosmetics, and cosmetic products (cosmetics) which contain at least one such extract.

The mirabelle is the fruit of a tree (mirabelle tree) which belongs to a very common genus (Prunus type, Rosaceae family) which includes especially the almond (*prunus amygdalus*) and the following edible fruits: apricot (*prunus armeniaca*), cherry (*prunus avium, prunus cerasus*), the peach (*prunus persica*), plums (*prunus domestica*, a genus which contains many subgenera). The exact botanical designation of the plants is prunus, of the subgenus Punophora, of the genus Insitisia, of the variety mirabelle.

The cultivation of the mirabelle tree which has taken place in northeast France since Roman times has developed out of the Mosel Departement, especially around the city of Metz.

Thus in 1994 the mirabelle harvest in France was estimated at seven million tons and the current primary sales areas of the fruit are canning factories (70%), distilleries (17%), fresh fruit consumption (12%).

A comparison of the oil content of the seeds of the different fruits of the Prunus genus except for the mirabelle and their fatty acid composition has been published in the "Characterization of the seed oil and meal from apricot, cherry, nectarine, peach and plum" Kamel B. S. & Kakuda Y., Journal of the American Oil Chemists' Society, 1992, vol. 69, no. 5, pp.492–494.

This article enables especially the statement that oils obtained from seeds and almonds of these different fruits have very similar fatty acid compositions and offer an interesting source for oleic acids (52–66%) and linoleic acids (28–35%).

Moreover it is known that almond seeds of edible fruits of the Prunus genus contain oils, of which some are used in cosmetics or pharmacology (sweet almonds, apricots).

Thus EP-A-0 105 876 discloses pharmaceutical compositions which contain especially a vegetable oil of the Prunus genus, preferably almond oil, and which are used to treat skin conditions (dermatological conditions).

In addition JP-A-01 313 414 and JP-A-01 038 014 relate to cosmetics which promote hair growth and which contain besides oil the extracts of plants, including *prunus persica* or *prunus armeniaca*.

But there is no publication known to the inventor which relates to the use of extract from mirabelle seeds in the area of cosmetics.

But the inventor has ascertained that lipid extracts which have been obtained from mirabelle seeds have special properties and very good tolerance, for which reason they can be directly used in cosmetic products (cosmetics).

In addition, mirabelle seeds, especially in the cultivation and processing areas of these fruits, offer an extensive and economical raw material, evaluation of which is of interest.

The main object of this invention is therefore the use of at least one lipid extract which is obtained from the seeds of the fruits of the mirabelle tree as an agent for preparation of a cosmetic product for locally acting (topical) use in the area of the care of the skin, lips, mucous membranes and/or appendages of the skin.

According to a first feature of the invention the lipid extract consists of oil or one or more lipid fractions which were extracted from the almond-shaped seeds within the pits of the fruits of the mirabelle tree by a process which was chosen in the group formed by extraction by hot or cold pressure, extraction by solvents and extraction by supercritical $CO_2$.

At least the indicated lipid extract can be added to the cosmetic product in raw, refined, deodorized or refined and deodorized form.

As examples for illustration, but not for limitation, two processes are described below relating to oil recovery from mirabelle seeds.

EXAMPLE 1

Roughly 4.04 kg cleaned and dried mirabelle seeds originating from canning factories are coarsely crushed and the resulting crushed mass is screened in order to obtain a fraction which is enriched with meal from the almond-shaped seeds within the pits of the fruit of the mirabelle tree; in this way 1.03 kg meal enriched with such seeds are obtained.

The meal is then extracted in the reflux in a reactor by 1.55 liters of hexane.

After cooling at room temperature the hexane extract is recovered by filtering and then concentrated by a rotary evaporator in order to obtain an oily fraction which at 45° C. is sent to a drying oven to eliminate the traces of the solvent.

In this way 105 ml slightly cloudy, yellow raw oil which has a pleasant almond scent and 0.31% oleic acid content is obtained.

The yield with respect to the weight of this extraction is 2.60% relative to the seeds and 10.2% with reference to the meal thus enriched.

EXAMPLE 2

4.64 kg dried, crushed seeds from distilleries are extracted in a reactor and in reflux for one hour with 4.64 liters of hexane. The hexane extract is then processed as in example 1.

This yields 298 ml of cloudy, dark yellow oil which has a strong odor of fermented fruit and a high oleic acid content which is 17.08% by weight.

Then the oil is subjected to a refinement and deodorization process using techniques which are familiar to one skilled in the art in order to reach 169 ml of yellow, odorless oil with 0.15% oleic acid content.

The yields by weight with respect to the oil are consequently 6.42% raw oil/seeds and 3.6% with reference to the refined, deodorized oil.

According to a first embodiment method of the invention at least the indicated lipid extract obtained from mirabelle seeds is added to a cosmetic product for the skin, the lips and/or the mucous membranes as a softening, moisturizing agent which imparts freshness and a radiant shine to the skin.

According to a second embodiment method of the invention the indicated lipid extract is added to a cosmetic product for the extremities of the skin, especially for the hair as a softening moisturizer to impart shine to the hair and to facilitate detangling and styling.

But besides the aforementioned embodiment methods the aforementioned lipid extract(s) can also be added as the sole or not the sole active agent to a product or a cosmetic composition for local (topical) simultaneous use for the skin, lips, mucous membranes and the extremities of the skin.

The advantageous properties of the lipid extracts were proven and quantitatively determined by the various tests, the implementation and results of which are explained below.

Evaluation of the Softening Action which Facilitates Styling

The action of treatment with a shampoo which has been proportioned to 1.5% mirabelle oil and which was prepared according to example 2 is quantitatively evaluated by easier styling and detangling of human hair compared to a shampoo placebo.

The principle of the method consists in measuring the force which opposes combing through one strand of hair at a constant rate.

The evaluated parameters are the maximum force (N) which corresponds to the plotted force when combing through the hair ends and the work (Nmm) which is done during styling and which corresponds to the area under the force-lengthening curve.

Measurements were taken before and after treatment with the shampoo placebo (5 strands) or with the shampoo proportioned to 1.5% mirabelle oil (5 strands) under completely identical assumptions.

The results shown on FIG. 1 of the attached drawings (action on the property of the hair to be easily styled: on the average five tests +/− SEM/test Wilcoxon for series summarized in pairs) show that treatment with the shampoo placebo does not significantly influence the parameters of the styling force (NS).

In contrast, treatment with the shampoo proportioned to 1.5% mirabelle oil produces softer hair, resulting in a 34% reduction (*: significant difference) of work during styling and 29% reduction (*:significant difference) of the maximum force.

Evaluation of the Softening Action on the Skin Ex Vivo

The lubricant-like and softening action of the cosmetic active agent is manifested in the biophysical aspect by reduced friction between the skin and the material brought into contact with it.

The reduction of friction can be attributed to the surface changes of a physical type, which result in soft, supple, and satiny skin.

The softening action of the oil which was obtained from the mirabelle seed and which was prepared according to example 2 was proven by the evaluation test of friction on the human skin ex vivo in comparison to a reference product (Eutanol G from HENKEL) one hour after treatment and by a frictiometer of the so-called altered Comaisch type.

The operating principle of this apparatus is as follows: a constant force is applied to the skin by a sliding shoe which is rotated at a controlled speed and under controlled pressures, the moment of friction being measured and enabling computation of the coefficient of friction of the slide shoe on the skin. The coefficient of friction depends on the surface constitution of the skin, especially on its moisture content and its softness.

Friction was measured at various rotational speeds by exerting the standard pressure of a probe on the skin.

The results are shown in FIG. 2 (measurement averages +/− SEM) which represents the effects on the properties of friction of the human skin ex vivo; the results prove that treatment with Eutanol G causes a slight reduction of the friction between 17% and 8% depending on the rotational speed.

The reduction of friction is much greater (between 43% and 26%) in the case of treatment with mirabelle oil.

Evaluation of the Moisturizing Capacity

The moisturizing action of the mirabelle oil prepared as per examples 1 and 2 was measured by conductometry 21 hours after the standardized application (4 mg/cm$^2$) on the antero-inner side of the underarm of a volunteer; then a 15% to 20% increase of skin moisture (cutaneous hydration) is established.

Fresh and Radiating Glow of the Complexion

These effects have been evaluated by brillantometry on the antero-inner side of the underarm 5 minutes after standardized application (4 mg/cm$^2$) of the oil; a very good shining action was ascertained which is better than that by a reference oil (jojoba oil) with little improvement of the complexion.

Sensory tests on the skin also prove that the oil is very blanketing, with a strong spreading capacity, forms films very easily and leaves a very shiny film on the skin; this film remains 15 minutes after application by also imparting a very persistent feeling of softness.

These various tests prove that the oil or the lipid extracts of the seed and quite especially of the almond-shaped seed of the mirabelle offer special properties which make then useful for application in cosmetics, especially for dermatological products which are intended for the skin, lips, and appendages of the skin (especially the hair) and especially as a softening and moisturizing agent which contributes to sheen and which improves the radiant luster of the skin, and as agents which facilitate styling.

The objective of this invention is likewise a cosmetic product for the locally acting (topical) use for the skin, the mucous membranes and/or the lips, characterized in that it contains between 0.05% and 100% by weight, preferably between 1% and 10% by weight of at least one lipid extract obtained from the almond of the seed of the fruit of the mirabelle tree as an active, softening and moisturizing agent which improves the freshness of the complexion and its radiant glow.

Moreover the invention likewise relates to a cosmetic product for locally acting (topical) use for the appendages of the skin, especially for the hair, characterized in that it contains between 0.05% and 100% by weight and preferably between 1% and 10% by weight of at least one lipid extract obtained from the almond-shaped seed of the fruit of the mirabelle tree as an active, softening and moisturizing agent which improves the luster of the hair and facilitates its detangling and styling.

The aforementioned extracts can be used for applications in the care, hygiene and protection of skin (products for the face and body, daytime and nighttime cosmetics, sunscreens, make-up, hand and lip protection agents) but also in the area of the care and treatment of hair (hair tonic, shampoo, creams, foams, protective agents, repair, softening, film-forming agents, and light protection agents).

Various cosmetic products or compositions which contain at least one lipid extract obtained from mirabelle seeds are described below as unrestricted examples for practical embodiments of the invention.

EXAMPLE 1

A cosmetic product in the form of a moisturizer for dry hair as claimed in the invention can for example have a composition by weight which is formed by the following fractions A and B, as are described below.

| Fraction A: | |
|---|---|
| cetyl alcohol | 2.00% |
| paraffin oil | 2.00% |
| sorbitan stearate | 2.00% |
| mirabelle oil (obtained as in example no. 1) | 2.00% |
| Fraction B: | |
| glycerin | 2.00% |
| laneth-20 | 1.00% |
| cetrimonium chloride | 2.00% |
| preservative | qs |
| distilled water | qsb 100.00% |

The process for preparation and production of the aforementioned moisturizer for dry hair consists mainly in allowing all components of fraction A (fatty phase) to melt at 75° while stirring, heating the fraction B (water-containing phase) to 90° C. by dissolving various components at this temperature, shaking fraction A into fraction B and finally cooling the mixture while stirring until perfect homogeneity is reached.

EXAMPLE 2

A cosmetic product in the form of a shampoo for styling, detangling and softening as claimed in the invention can have for example a composition by weight which is formed by the following fractions A, B, C, D, E, F, G, H, and I as is given below:

| Fraction A: | |
|---|---|
| water | 45.500% |
| hydroxypropyl guar hydroxypropyltrimonium chloride | 0.400% |
| Fraction B: | |
| mixed polymerisate acrylate/C10–30 alkyl acrylate | 0.600% |
| water | 19.400% |
| Fraction C: | |
| sodium lauryl sulfate (and) lauryl polyglucose | 25.000% |
| Fraction D: | |
| LS38 ATA stabilizer (Laboratoires Sérobiologiques) | 0.300% |
| Fraction E: | |
| titanium dioxide (and) mica | 0.600% |
| Fraction F: | |
| triethanolamine (20% aqueous solution) | 4.000% |
| Fraction G: | |
| dimethicone | 1.500% |
| mirabelle oil (obtained as per example No. 2) | 2.000% |
| Fraction H: | |
| CG cathone (octhilinone) | 0.100% |
| Fraction I: | |
| perfume | 0.600% |

The process for preparation and production of the aforementioned shampoos consists mainly in preparation of fraction A at 82° C., in adding fractions B, C, and D to A with turbine stirring, afterwards in adding fractions E and F with turbine stirring, afterwards in cooling to 30° C. and finally in adding fractions G, H and I with planetary stirring.

EXAMPLE 3

A cosmetic product in the form of a medicinal hair balm for dry, dull and worn-out hair as claimed in the invention can have for example a composition by weight which is formed from the following fractions A, B, and C as is given below.

| Fraction A: | |
|---|---|
| glycerin stearate (and) PEG-100 stearate | 2.500% |
| dimethicone | 1.000% |
| cyclomethicone | 2.000% |
| mirabelle oil (obtained as in example no. 1) | 3.000% |
| Fraction B: | |
| water | 85.800% |
| Elestab 388 (registered trademark) | 2.500% |
| guar-hydroxypropyltrimonium chloride | 1.000% |
| guar gum | 1.000% |
| Fraction C: | |
| sodium citrate (20% aqueous solution) | 0.600% |
| citric acid (10% aqueous solution) | 0.600% |

The process for preparation and production of the aforementioned balm consists mainly in preparing fraction A at 75° C., in separate preparation of fraction B at 75° C. with turbine stirring, in adding fraction A to fraction B with turbine stirring, cooling of the mixture to 60° C. with turbine stirring, afterwards with planetary stirring and finally at room temperature, adjusting the pH to 6.0.

EXAMPLE 4

A cosmetic product in the form of a lipstick to intensify the shine of the lips as claimed in the invention can have for example a composition by weight as is given below.

| ricinus oil | 30.00% |
|---|---|
| glycerin stearate | 43.00% |
| isopropyl myristate | 8.00% |
| paraffin oil | 5.00% |
| mirabelle oil (obtained as per example No. 2) | 3.00% |
| vaseline | 4.00% |
| carnauba wax | 4.00% |
| suint alcohol | 3.00% |

The process for preparing and producing the aforementioned lipstick consists mainly in heating all fatty bodies while stirring to 90° C., pouring the melted and homogenous mass into a mold and finally cooling and completing the preparation using classical technique.

EXAMPLE 5

A cosmetic product in the form of a cream oil in softening and moisturizing water which increases the shine of the skin as claimed in the invention can have for example a composition by weight which is formed from the following fractions A, B, and C as is given below.

| Fraction A: | |
|---|---|
| triceteareth-4 phosphate | 3.00% |
| polyglycerin-2-PEG-4 stearate | 8.00% |
| paraffin oil | 7.00% |
| mirabelle oil (obtained as in example no. 1) | 5.00% |
| isopropyl palmitate | 8.00% |
| stearyl heptanoate | 2.00% |

-continued

| Fraction B: | |
|---|---|
| methyl parabene | 0.20% |
| glycol propylene | 2.00% |
| imidazolidinyl carbonide | 0.30% |
| water | 64.20% |
| Fraction C: | |
| perfume | 0.30% |

The process for preparing and producing the aforementioned creme consists mainly in heating fraction A to 80° C. while stirring, in heating fraction B to 70° C., pouring fraction A into fraction B with turbine stirring, afterwards in gradually cooling with planetary stirring, afterwards in adding fraction C at roughly 45° C. and finally in stopping the stirring after room temperature has been reached again.

Of course the invention is not limited to the described embodiment methods shown in the attached drawings. Changes are possible, especially with respect to the composition of the various elements or by replacing technical equivalents without therefore departing from the scope of protection of the invention.

What is claimed is:

1. A method for preparation of a cosmetic product for topical use in the area of the care of the skin, lips, mucous membrane and/or appendages of the skin comprising the step of providing at least one lipid extract which is obtained from the seeds of the fruits of the mirabelle tree as an agent, wherein said at least one lipid extract is added to the cosmetic product in raw, refined, deodorized or refined and deodorized form.

2. The method as claimed in claim 1, wherein the lipid extract consists of oil or of one lipid fraction or lipid fractions which were obtained from the almonds of the seeds of the fruit of the mirabelle tree by a process which was chosen in the group formed by extraction by pressure, extraction by solvents and extraction by supercritical $CO_2$.

3. The method as claimed in claim 1 wherein at least one indicated lipid extract is added to a cosmetic product for the skin, lips and/or mucous membranes as agents for softening and moisturizing and for improving the freshness and radiant glow of the complexion.

4. The method as claimed in claim 1 wherein at least the indicated lipid extract is added to a cosmetic product for the extremities or appendages of the skin and especially for the hair as an agent for softening, moisturizing and improving the sheen and for easier detangling and styling of the hair.

5. Cosmetic product for topical use for locally acting (topical) use for the skin, the mucous membranes and/or the lips, wherein it contains between 0.05% and 100% by weight of at least one lipid extract obtained from the almond-shaped seed within the pit of the fruit of the mirabelle tree as an active agent for softening, moisturizing and improving the freshness of the complexion and its radiant glow, wherein said at least one lipid extract is added to the cosmetic product in raw, refined, deodorized or refined and deodorized form, said at least one lipid extract being admixed with a cosmetically acceptable carrier.

6. Cosmetic product for topical use for locally acting (topical) use for the extremities or appendages of the skin wherein it contains between 0.05% and 100% by weight of at least one lipid extract obtained from the almond-shaped seed within the pit of the fruit of the mirabelle tree as an active agent for softening, moisturizing and improving the sheen of the hair and enabling easier detangling and styling, wherein said at least one lipid extract is added to the cosmetic product in raw, refined, deodorized or refined and deodorized form, said at least one lipid extract being admixed with a cosmetically acceptable carrier.

7. Cosmetic product as claimed in claim 5, wherein said at least one lipid extract is present in the amount between 1% and 10% by weight.

8. Cosmetic product as claimed in claim 6, wherein said at least one lipid extract is present in the amount between 1% and 10% by weight.

* * * * *